United States Patent [19]

Fischer

[11] Plant 5,100

[45] Sep. 6, 1983

[54] AFRICAN VIOLET NAMED CAMELOT

[75] Inventor: Arnold W. Fischer, Hanover, Fed. Rep. of Germany

[73] Assignee: Pan American Plant Company, Parrish, Fla.

[21] Appl. No.: 252,838

[22] Filed: Apr. 10, 1981

[51] Int. Cl.[3] ..... A01H 5/00

[52] U.S. Cl. ..... Plt./69

[58] Field of Search ..... Plt./69

*Primary Examiner*—James R. Feyrer

*Attorney, Agent, or Firm*—Chas. W. Rummler

[57] ABSTRACT

A new and distinct African Violet cultivar distinguished by its profuse production of shell pink flowers which have striking dark pink eyes and which comprise three large and two smaller petals. This plant has a vigorous growth habit and the flowers are borne on strong, erect stems which present them as a bouquet above a relatively flat bed of medium green foliage.

4 Drawing Figures

BACKGROUND OF THE NEW PLANT

This new African Violet plant originated as a seedling of unknown parentage growing in a field of violet plants maintained in greenhouse at Fallbrook, Calif., for breeding purposes. I discovered this plant at Fallbrook in 1977 and because of its lovely shell pink flowers with their distinctive dark pink eyes, I selected this plant for propagation and test and for that purpose, I reproduced the discovery plant, by means of cuttings, at Fallbrook with very favorable results. Subsequently, propagation of this plant was extended through several successive generations at Fallbrook, which demonstrated that the novel characteristics of the plant would hold true from generation to generation and appeared to be firmly fixed. This new plant is now being propagated on a commercial scale at West Chicago, Ill., and at Parrish, Fla.

DESCRIPTION OF THE DRAWINGS

This new violet plant is illustrated by the accompanying drawings, of which sheet 1 is a photographic view of a potted plant in full bloom, sheet 2 is a photographic print showing a full face view of a flower of this variety which has been hand-painted to show the true flower colors, and sheets 3 and 4 are prints of machine copies of the front and back sides, respectively, of typical leaves of this new plant.

DESCRIPTION OF THE NEW PLANT

The following is a detailed description of this new African Violet cultivar based upon observations made in greenhouse at West Chicago, Ill., the color designations being according to The R.H.S. Colour Chart published by The Royal Horticultural Society of London, England.

THE PLANT

Origin: Seedling.
Parentage: Unknown.
Classification:
- *Botanic.*—Saintpaulia Ionantha.
- *Commercial.*—African Violet.

Form: Compact and of rosette shape.
Growth habit: Strong and vigorous.
Growth rate: Rapid.

Foliage:
- *Quantity.*—Moderate, with about 16 leaves.
- *Size of leaf.*—Length — From insignificant to about 90 mm. Width — From insignificant to about 80 mm.
- *Shape of leaf.*—Oval with obtuse tip, oblique base, and repand margin.
- *Texture.*—Pubescent.
- *Color.*—Upper side — 137A. Under side — 138D.
- *Ribs and veins.*—Pinnate.
- *Rachis.*—Length — From insignificant to about 90 mm.

THE BUD

Form: Globular.
Size: Average with various diameters and lengths.
Opening rate: Typical violet.
Color of petals:
- *When sepals first divide.*—62B.
- *When petals begin to unfurl.*—62B.

Sepals:
- *Number.*—Five.
- *Shape.*—Lanceolate and branched. When the flowers open, the sepals become flat.
- *Color.*—Inside — 148A. Outside — 148A.
- *Striae.*—None.

Calyx:
- *Size.*—Small.
- *Shape.*—Calyx splits to star shape.
- *Aspect.*—Hairy.

Peduncle:
- *Character.*—Erect and rigid.
- *Length.*—From insignificant to about 85 mm.
- *Color.*—161A.

THE FLOWER

Blooming habit: Intermittent.
Flowering character: The plant flowers profusely.
Flower size: Medium.
- *Diameter.*—About 30 to 45 mm.
- *Depth.*—Flat.

Borne: As a cyme.
Shape: When bloom first opens, the flower is cup-shaped and as the bloom matures, it becomes flat.
Petalage:
- *Number of petals.*—Five.
- *Arrangement.*—Sympetalous.

*Form.*—Rotate-zygomorphic with rounded apex and entire margins.

*Texture.*—Soft.

*Color.*—Main body of petal — 70B. At throat — 70A. Marginal edges — 70C. Reverse side — 70B.

*Petaloids.*—Number: From none to as many as three. Size: Insignificant.

Flower stem:

*Length.*—From insignificant to about 85 mm.

*Character.*—Upright and strong.

*Color.*—161A.

Discoloration after full bloom: The flower fades to 70D.

Persistence: The flowers hang on and dry.

Fragrance: None.

Lasting quality: From 10 to 20 days on the plant.

REPRODUCTIVE ORGANS

Stamens:

*Anthers.*—Number: Two. Arrangement: Monadelphous. Size: About 3 mm. square. Color: Yellow.

*Filaments.*—Length: About 3 mm. Color: Whitish yellow.

*Pollen.*—Color — Yellow.

Pistils:

*Number.*—One.

*Style.*—Length: About 8 mm. Color: 70C.

*Stigma.*—Color — Whitish.

Ovaries: Hypogynous and tomentose.

This African Violet cultivar is distinguished by its shell pink zygomorphic flowers which have striking dark pink eyes surrounded by three large and two smaller petals. The plant has a vigorous growth rate and produces a profusion of blooms which are borne in a bouquet centered above a bed of green foliage.

I claim:

1. A new and distinct African Violet cultivar, substantially as herein shown and described, characterized by its production of a profusion of shell pink flowers having striking dark pink eyes and excellent keeping quality, the zygomorphic flower having three large and two smaller petals.

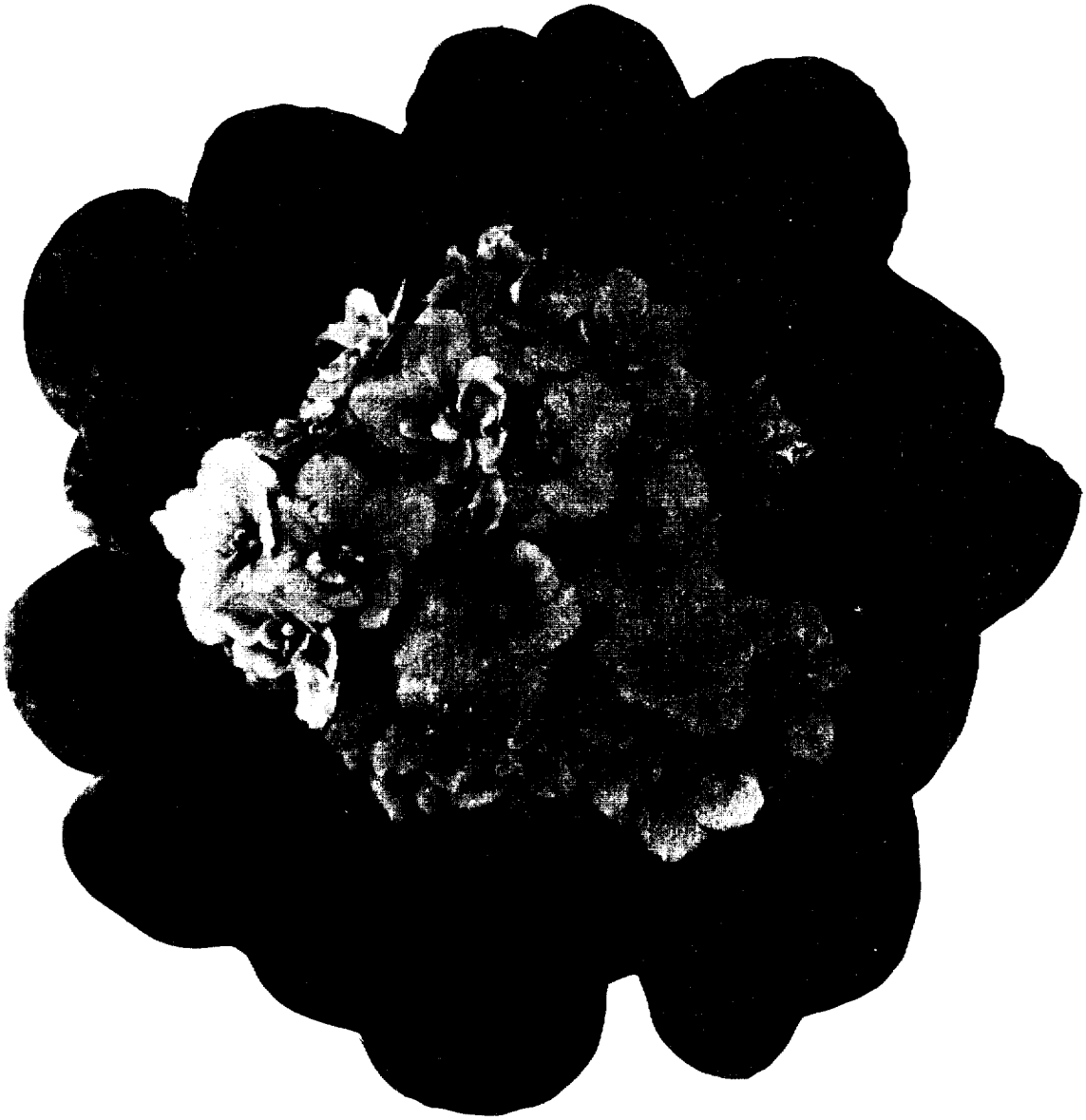

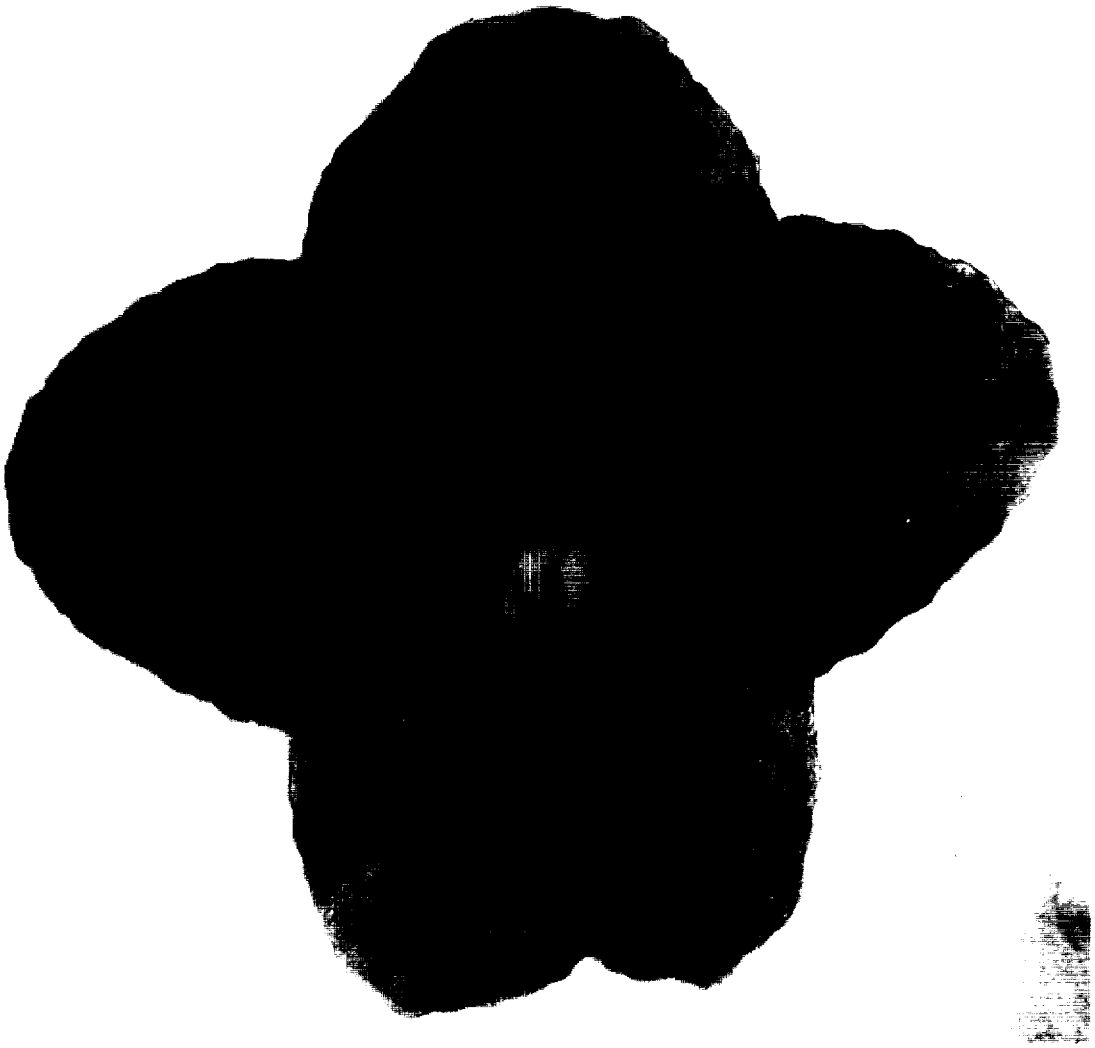

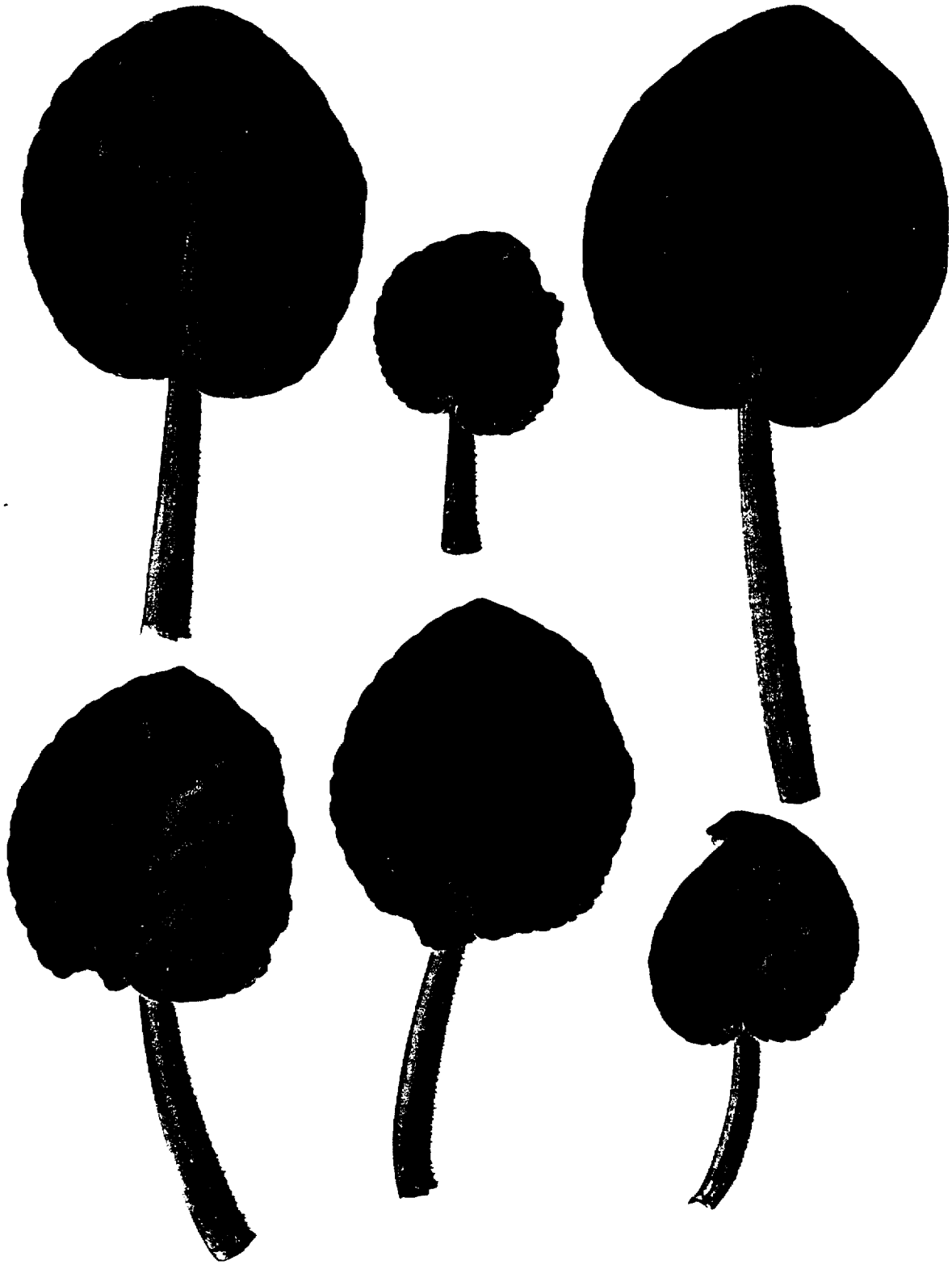

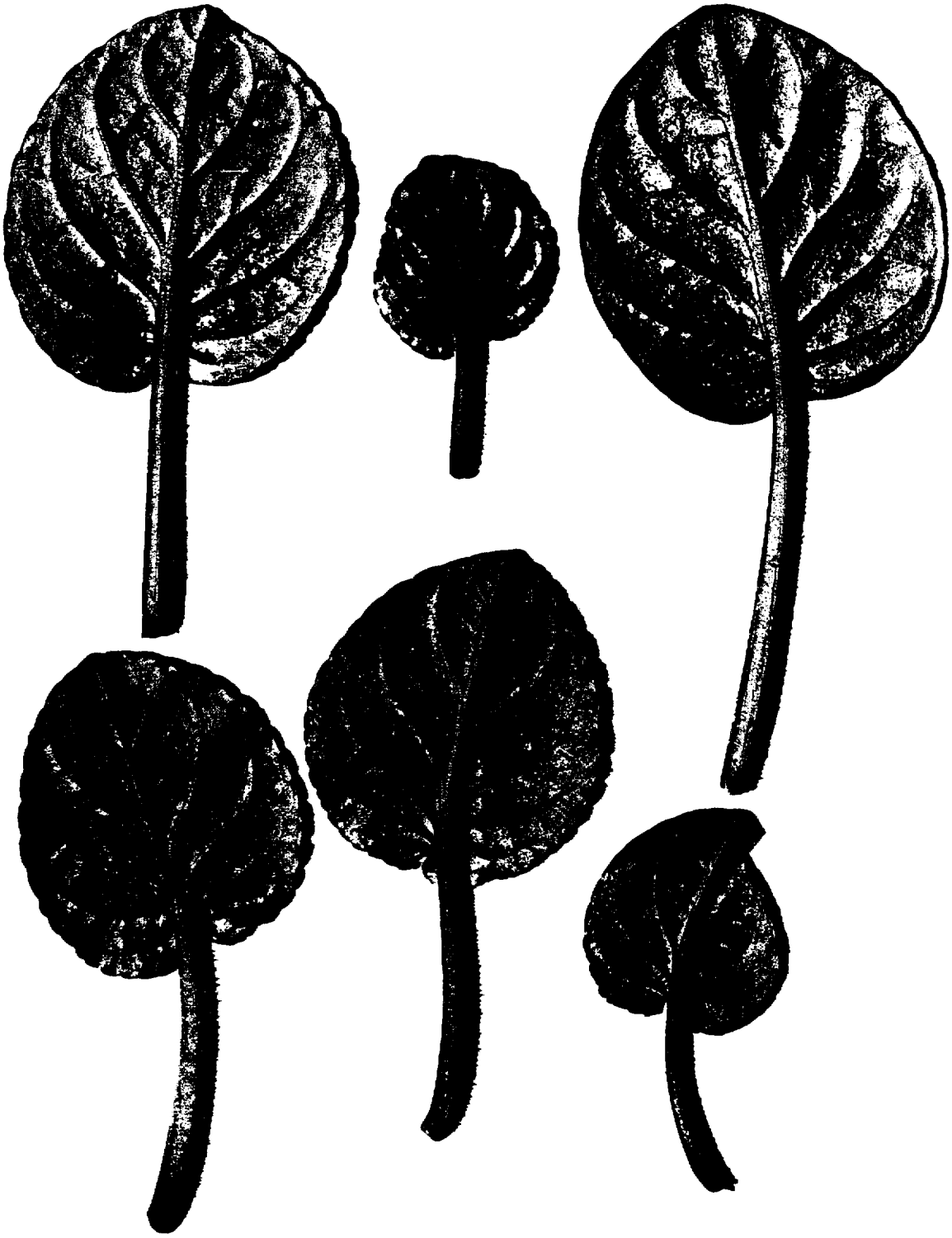

* * * * *